United States Patent
Shapland et al.

(10) Patent No.: US 9,295,816 B2
(45) Date of Patent: Mar. 29, 2016

(54) CATHETER WITH DISTAL AND PROXIMAL PORTS

(75) Inventors: James Edward Shapland, St. Paul, MN (US); Christopher G. Quinn, Minneapolis, MN (US); Rodney L Houfburg, Prior Lake, MN (US); Tuan Minh Doan, Burnsville, MN (US)

(73) Assignee: Osprey Medical, Inc., Minnetonka, MN (US)

( * ) Notice: Subject to any disclaimer, the term of this patent is extended or adjusted under 35 U.S.C. 154(b) by 0 days.

(21) Appl. No.: 12/928,327

(22) Filed: Dec. 7, 2010

(65) Prior Publication Data

US 2011/0172558 A1    Jul. 14, 2011

Related U.S. Application Data

(60) Provisional application No. 61/283,958, filed on Dec. 9, 2009.

(51) Int. Cl.
| | |
|---|---|
| *A61B 5/15* | (2006.01) |
| *A61M 25/10* | (2013.01) |
| *A61M 1/36* | (2006.01) |
| *A61M 1/00* | (2006.01) |
| *A61M 25/00* | (2006.01) |

(52) U.S. Cl.
CPC ............ *A61M 25/10* (2013.01); *A61M 1/3653* (2013.01); *A61M 1/0031* (2013.01); *A61M 25/007* (2013.01); *A61M 2025/1052* (2013.01)

(58) Field of Classification Search
CPC . A61M 1/3653; A61M 1/0031; A61M 25/10; A61M 25/007; A61M 27/00; A61M 2025/1052
USPC ............ 600/573, 578, 574, 576, 584; 604/35, 604/103.05, 508
See application file for complete search history.

(56) References Cited

U.S. PATENT DOCUMENTS

| | | | |
|---|---|---|---|
| 3,931,815 A * | 1/1976 | Takatsuki | ........................ 600/577 |
| 4,054,137 A | 10/1977 | Lee et al. | |
| 4,581,017 A | 4/1986 | Sahota | |
| 4,592,341 A | 6/1986 | Omagari et al. | |
| 4,795,427 A | 1/1989 | Helzel | |
| 4,838,872 A * | 6/1989 | Sherlock | ........................ 604/319 |
| 4,968,306 A * | 11/1990 | Huss | .................. A61M 25/007 |
| | | | 604/264 |
| 4,969,470 A | 11/1990 | Mohl et al. | |
| 5,069,662 A | 12/1991 | Bodden | |
| 5,338,662 A | 8/1994 | Sadri | |
| 5,423,745 A | 6/1995 | Todd et al. | |
| 5,494,822 A | 2/1996 | Sadri | |
| 5,807,311 A * | 9/1998 | Palestrant | ........................ 604/28 |
| 5,807,318 A | 9/1998 | St. Goar et al. | |

FOREIGN PATENT DOCUMENTS

| | | |
|---|---|---|
| DE | 10102045 | 1/2003 |
| EP | 0301854 | 2/1989 |

(Continued)

OTHER PUBLICATIONS

Alfayoumi, F. et al., "The No-Reflow Phenomenon: Epidemiology, Pathophysiology, and Therapeutic Approach," Reviews in Cardiovascular Medicine, vol. 6, No. 2, pp. 72-83 (2005).

(Continued)

*Primary Examiner* — Michael C Stout

(57) ABSTRACT

A catheter system including a collection member having an occlusion member and collection ports. At least one collection port being located distal to the occlusion member, and least one collection port being located proximal to the occlusion member.

7 Claims, 13 Drawing Sheets

(56) References Cited

U.S. PATENT DOCUMENTS

| | | | |
|---|---|---|---|
| 5,807,322 A | 9/1998 | Lindsey et al. | |
| 5,810,757 A * | 9/1998 | Sweezer, Jr. | A61M 1/10 604/523 |
| 5,813,842 A | 9/1998 | Tamari | |
| 5,843,016 A * | 12/1998 | Lugnani | A61N 1/306 604/21 |
| 5,871,464 A | 2/1999 | Tryggvason et al. | |
| 5,871,465 A | 2/1999 | Vasko | |
| 6,021,340 A | 2/2000 | Randolph et al. | |
| 6,080,170 A | 6/2000 | Nash et al. | |
| 6,093,392 A | 7/2000 | High et al. | |
| 6,110,139 A | 8/2000 | Loubser | |
| 6,152,141 A | 11/2000 | Stevens et al. | |
| 6,186,146 B1 | 2/2001 | Glickman | |
| 6,251,093 B1 | 6/2001 | Valley et al. | |
| 6,254,563 B1 | 7/2001 | Macoviak et al. | |
| 6,295,990 B1 | 10/2001 | Lewis et al. | |
| 6,342,214 B1 | 1/2002 | Tryggvason et al. | |
| 6,376,471 B1 | 4/2002 | Lawrence, III et al. | |
| 6,398,752 B1 | 6/2002 | Sweezer et al. | |
| 6,481,439 B1 | 11/2002 | Lewis et al. | |
| 6,500,158 B1 | 12/2002 | Ikeguchi | |
| 6,508,777 B1 | 1/2003 | Macoviak et al. | |
| 6,554,819 B2 | 4/2003 | Reich | |
| 6,558,349 B1 | 5/2003 | Kirkman | |
| 6,569,147 B1 | 5/2003 | Evans et al. | |
| 6,585,716 B2 | 7/2003 | Altman | |
| 6,595,963 B1 | 7/2003 | Barbut | |
| 6,638,264 B1 | 10/2003 | Tryggvason et al. | |
| 6,638,268 B2 | 10/2003 | Niazi | |
| 6,673,039 B1 | 1/2004 | Bridges et al. | |
| 6,689,090 B1 | 2/2004 | Tryggvason et al. | |
| 6,699,231 B1 | 3/2004 | Steman et al. | |
| 6,726,651 B1 | 4/2004 | Robinson et al. | |
| 6,935,344 B1 | 8/2005 | Aboul-Hosn et al. | |
| 6,980,843 B2 | 12/2005 | Eng et al. | |
| 6,992,070 B2 | 1/2006 | Donahue et al. | |
| 7,211,073 B2 | 5/2007 | Fitzgerald et al. | |
| 7,300,429 B2 | 11/2007 | Fitzgerald et al. | |
| 7,331,922 B2 | 2/2008 | Mohl | |
| 7,363,072 B2 | 4/2008 | Movahed | |
| 7,722,596 B2 | 5/2010 | Shapland et al. | |
| 8,152,786 B2 | 4/2012 | Shapland et al. | |
| 2001/0052345 A1 | 12/2001 | Niazi | |
| 2002/0062121 A1 | 5/2002 | Tryggvason et al. | |
| 2002/0077595 A1 | 6/2002 | Hundertmark et al. | |
| 2002/0091349 A1 | 7/2002 | Reich | |
| 2002/0099254 A1 | 7/2002 | Movahed | |
| 2002/0107504 A1 | 8/2002 | Gordon | |
| 2002/0165598 A1 | 11/2002 | Wahr et al. | |
| 2002/0169436 A1 | 11/2002 | Gurm et al. | |
| 2003/0004434 A1 * | 1/2003 | Greco | A61B 5/205 600/561 |
| 2003/0004452 A1 * | 1/2003 | Lenker | A61M 1/3653 604/4.01 |
| 2003/0036728 A1 * | 2/2003 | Samson | A61B 17/12045 604/103.01 |
| 2003/0138350 A1 | 7/2003 | Macoviak | |
| 2003/0163081 A1 | 8/2003 | Constantz et al. | |
| 2003/0191434 A1 | 10/2003 | Dorros et al. | |
| 2003/0199917 A1 | 10/2003 | Knudson et al. | |
| 2003/0236533 A1 | 12/2003 | Wilson et al. | |
| 2004/0002159 A1 | 1/2004 | Xiao et al. | |
| 2004/0030286 A1 | 2/2004 | Altman | |
| 2004/0099596 A1 | 5/2004 | Naghavi et al. | |
| 2004/0102732 A1 | 5/2004 | Naghavi et al. | |
| 2004/0102766 A1 | 5/2004 | Poleo, Jr. | |
| 2004/0147864 A1 * | 7/2004 | Lenker | A61M 1/3653 604/4.01 |
| 2004/0210239 A1 | 10/2004 | Nash et al. | |
| 2004/0254523 A1 | 12/2004 | Fitzgerald et al. | |
| 2005/0010189 A1 | 1/2005 | Toomey et al. | |
| 2005/0124969 A1 * | 6/2005 | Fitzgerald et al. | 604/508 |
| 2005/0137539 A1 * | 6/2005 | Biggie | A61M 1/0096 604/313 |
| 2005/0192548 A1 | 9/2005 | Dolliver et al. | |
| 2005/0197531 A1 | 9/2005 | Cabiri et al. | |
| 2005/0226855 A1 | 10/2005 | Alt et al. | |
| 2005/0256441 A1 | 11/2005 | Lotan et al. | |
| 2005/0273014 A1 | 12/2005 | Gianchandani et al. | |
| 2006/0013772 A1 * | 1/2006 | LeWinter | A61M 1/3621 424/9.52 |
| 2007/0038170 A1 * | 2/2007 | Joseph | A61M 1/3667 604/6.16 |
| 2007/0078352 A1 | 4/2007 | Pijls | |
| 2007/0118072 A1 | 5/2007 | Nash | |
| 2007/0135779 A1 * | 6/2007 | Lalomia | A61M 1/0001 604/319 |
| 2007/0203445 A1 | 8/2007 | Kaye et al. | |
| 2007/0255162 A1 | 11/2007 | Abboud et al. | |
| 2008/0021314 A1 | 1/2008 | Movahed | |
| 2008/0108960 A1 * | 5/2008 | Shapland | A61M 1/0031 604/321 |
| 2008/0125698 A1 | 5/2008 | Gerg et al. | |
| 2008/0125746 A1 | 5/2008 | Shapland et al. | |
| 2008/0306425 A1 | 12/2008 | Al-Rashdan | |
| 2009/0018526 A1 | 1/2009 | Power | |
| 2009/0069829 A1 | 3/2009 | Shturman | |
| 2009/0187131 A1 | 7/2009 | Fitzgerald et al. | |
| 2009/0234321 A1 | 9/2009 | Shapland et al. | |
| 2009/0312696 A1 * | 12/2009 | Copa | A61M 25/007 604/43 |
| 2010/0041984 A1 | 2/2010 | Shapland et al. | |
| 2010/0042069 A1 | 2/2010 | Shapland et al. | |
| 2010/0082004 A1 | 4/2010 | Shapland et al. | |
| 2010/0168564 A1 | 7/2010 | Shapland et al. | |
| 2010/0274173 A1 | 10/2010 | Shapland et al. | |
| 2011/0015558 A1 | 1/2011 | Kaye et al. | |
| 2011/0082489 A1 * | 4/2011 | Davies, Jr. | A61M 25/10 606/192 |
| 2011/0190727 A1 * | 8/2011 | Edmunds | A61F 2/958 604/509 |
| 2011/0224606 A1 * | 9/2011 | Shome | A61M 25/1018 604/96.01 |
| 2013/0079697 A1 | 3/2013 | Kaye | |
| 2014/0188062 A1 | 7/2014 | James et al. | |
| 2015/0182684 A1 | 7/2015 | Kaye et al. | |
| 2015/0190564 A1 | 7/2015 | Kaye | |

FOREIGN PATENT DOCUMENTS

| | | |
|---|---|---|
| EP | 0150960 | 1/1990 |
| EP | 0526102 | 4/1998 |
| EP | 1859826 | 11/2007 |
| GB | 2125487 | 3/1984 |
| JP | 2001-526071 | 12/2001 |
| WO | WO 89/01309 | 2/1989 |
| WO | WO 92/20387 | 11/1992 |
| WO | WO 98/31405 | 7/1998 |
| WO | WO 98/56440 | 12/1998 |
| WO | WO 99/29227 | 6/1999 |
| WO | WO 99/30765 | 6/1999 |
| WO | WO 99/31982 | 7/1999 |
| WO | WO 99/06097 | 12/1999 |
| WO | WO 01/00268 | 1/2001 |
| WO | WO 01/13983 | 3/2001 |
| WO | WO 01/83004 | 11/2001 |
| WO | WO 01/97901 | 12/2001 |
| WO | WO 02/060511 | 8/2002 |
| WO | WO 02/087677 | 11/2002 |
| WO | WO 03/070330 | 8/2003 |
| WO | WO 2004/083817 | 9/2004 |
| WO | WO 2005/027995 | 3/2005 |
| WO | WO 2005/082440 | 9/2005 |
| WO | WO 2006/004882 | 1/2006 |
| WO | WO 2006/042219 | 4/2006 |
| WO | WO 2007/002154 | 1/2007 |
| WO | WO 2007/143288 | 12/2007 |
| WO | WO 2008/122048 | 10/2008 |

OTHER PUBLICATIONS

Assali, A. et al., "Intracoronary Adenosine Administered During Percutaneous Intervention in Acute Myocardial Infarction and

(56) References Cited

OTHER PUBLICATIONS

Reduction in the Incidence of "No Reflow" Phenomenon," Catheterization and Cardiovascular Interventions, vol. 51, pp. 27-31 (2000).

de Lemos, J. et al., "New tools for assessing microvascular obstruction in patients with ST elevation myocardial infarction," Heart, vol. 90, pp. 119-120 (2004).

del Monte et al., "Improvement in Survival and Cardiac Metabolism After Gene Transfer of Sarcoplasmic Reticulum CA2+-ATPase in a Rat Model of Heart Failure", Circulation, 104(12): 1424-1429, 2001.

Hajjar et al., "Modulation of Ventricular Function Through Gene Transfer in Vivo", Proc. Natl. Acad. Sci., USA, 95: 5251-5256, 1998.

Kramer, c., "The prognostic significance of microvascular obstruction after myocardial infarction as defined by cardiovascular magnetic resonance," European Heart Journal, vol. 26, pp. 532-533 (2005).

Logeart, D. et al., "How to Optimize In Vivo Gene Transfer to Cardiac Myocytes: Mechanical or Pharmacological Procedures?", Human Gene Therapy, 12: 1601-1610, 2001.

Marzilli, M. et al., "Primary coronary angioplasty in acute myocardial infarction: Clinical correlates of the 'no reflow' phenomonen," International Journal o/Cardiology, vol. 65 (Suppl. I), pp. S23-S28 (1998).

Michishita, et al. "A Novel Contrast Removal System from the Coronary Sinus Using an Absorbing Column During Coronary Angiography in a Porcine Model", Journal of the American College of Cardiology, vol. 47, No. 9 (2006).

PCT International Search Report and Written Opinion in Application PCT/US2010/059505, mailed Mar. 14, 2011, 11pgs.

Resnic, F. et al., "No-reflow is an independent predictor of death and myocardial infarction after percutaneous coronary intervention," American Heart Journal, vol. 145, No. I, pp. 42-46 (2003).

Schrader, "Contrast Media-Induced Renal Failure: And Overview", Journal of Interventional Cardiology, vol. 18, No. 6, pp. 417-423 (2005).

Vogel, Robert et al., Transcatheter Coronary Artery Diagnostic Techniques, Texas Heart Insitute Journal, vol. 16, No. 3, dated 1989; 9 pgs.

* cited by examiner

MOVEABLE/ADJUSTABLE

CATHETER WITH DISTAL AND PROXIMAL PORTS

CROSS-REFERENCE TO RELATED APPLICATIONS

This application claims the benefit of U.S. Provisional Application No. 61/283,958, filed Dec. 9, 2009; which application is incorporated herein by reference.

FIELD OF THE TECHNOLOGY

This disclosure relates to catheters for collecting fluid from a blood vessel of a patient, and various methods associated with such devices. More particularly, this disclosure relates to catheters having more than one port for collecting fluid from a blood vessel, and various methods associated with such catheters.

BACKGROUND

Collection catheters are well known for collecting blood or other fluids from blood vessels of a patient, for example, for collecting blood from a coronary sinus or other coronary vein in a perfusion process. In addition to collecting blood in a perfusion process, blood may be collected from a coronary vein in an angiography procedure. Such procedures are used for assessing patency of coronary arteries. In such a procedure, a contrast medium is injected into a coronary artery for visualization of a suspected site of a coronary obstruction.

Contrast media may have significant health risks if permitted to flow systemically to the patient's organs. For example, renal dysfunction or failure may occur from such systemic delivery of a contrast media. Such failure is referred to as "contrast-induced nephropathy" or CIN. Accordingly, patients often undergo a contrast removal procedure to remove the contrast media from systemic delivery.

Blood collected in a contrast removal procedure may be processed to be re-admitted to the patient. However, it is more common for collected blood to be discarded. It is generally recognized that a limited amount (e.g., 150 milliliters to 200 milliliters) of blood may be safely removed from a patient and discarded.

Blood collection techniques include methods and apparatus for isolating blood flow in a vessel. This insures that primarily antegrade flow (i.e., the normal direction of blood flow in a vessel) is collected for a period of time for substantial collection of all contrast media or perfusate that is the object of collection.

Importantly, such isolation is employed to avoid collection of significant retrograde blood flow. Retrograde flow (in a direction opposite normal blood flow in a vessel) may occur, for example, where a catheter draws blood from a coronary sinus under suction. The suction may be such that blood in the right atrium flows retrograde and is drawn through the catheter. As a result, blood not laden with contrast media or perfusate is collected and possibly discarded. Since there are limits on how much blood may be discarded, it is desirable to minimize collecting and discarding blood not laden with contrast media or perfusate. Isolation or partial isolation is commonly achieved through use of balloon catheters. A balloon is inflated during periods of blood collection to seal against the wall of the blood vessel. Otherwise, the balloon is deflated to be spaced from the blood vessel wall.

In addition, individual anatomical differences may result in a coronary vein that empties into the coronary sinus, for example, proximal to the balloon or sealing member. Contrast or perfusate entering from such a vein may not be captured through a distal opening of the catheter.

Improvements to catheter systems and collection methods are needed, generally to, for example, collect contrast media or perfusate proximal to a sealing member, while minimizing the amount of retrograde flow collected. Further objectives of this disclosure may include systems and methods that additionally allow for selective and/or differential collection of contrast media or perfusate from various locals within a vessel and along a collection device.

SUMMARY

According to a preferred embodiment of the present invention, a method and apparatus are disclosed for collecting fluid from a blood vessel (such as a coronary sinus) of a patient. The method includes use of a catheter in the form of a collection member having an elongated, flexible tubular portion terminating at a distal end. At least one annular sealing or occlusion member (e.g., an inflatable balloon in a preferred embodiment) is secured to or provided on the tubular member spaced from the distal end. One or more collection lumens of the tubular member may have a fluid inlet distal to the sealing member as well as a proportionally sized fluid inlet immediately proximal to the sealing member. A proximal end of the tubular member may be adapted to be connected to a source of suction for applying suction to the one or more collection lumens. The method includes placing the distal end in a blood vessel with antegrade flow within the vessel flowing in a direction from the distal end toward the sealing member. The sealing member is deployed within the vessel. A vacuum is applied to the one or more collection lumens in an amount sufficient to draw blood and contrast media/perfusate from the vessel through the fluid inlets and into the collection lumen. Further the apparatus is designed so that a defined portion of the blood and contrast media/perfusate is drawn through the fluid inlets position proximal and distal to the sealing member. Control of the desired proportion coming from the proximal and distal fluid inlets is accomplished through specific apparatus designs.

A variety of examples of desirable product features or methods are set forth in part in the description that follows, and in part will be apparent from the description, or may be learned by practicing various aspects of the disclosure. The aspects of the disclosure may relate to individual features as well as combinations of features, including combinations of features disclosed in separate embodiments. It is to be understood that both the foregoing general description and the following detailed description are explanatory only, and are not restrictive of the claimed invention.

DETAILED DESCRIPTION

Reference will now be made in detail to exemplary aspects of the present disclosure that are illustrated in the accompanying drawings. Wherever possible, the same reference numbers will be used throughout the drawings to refer to the same or like parts.

Figure 1:
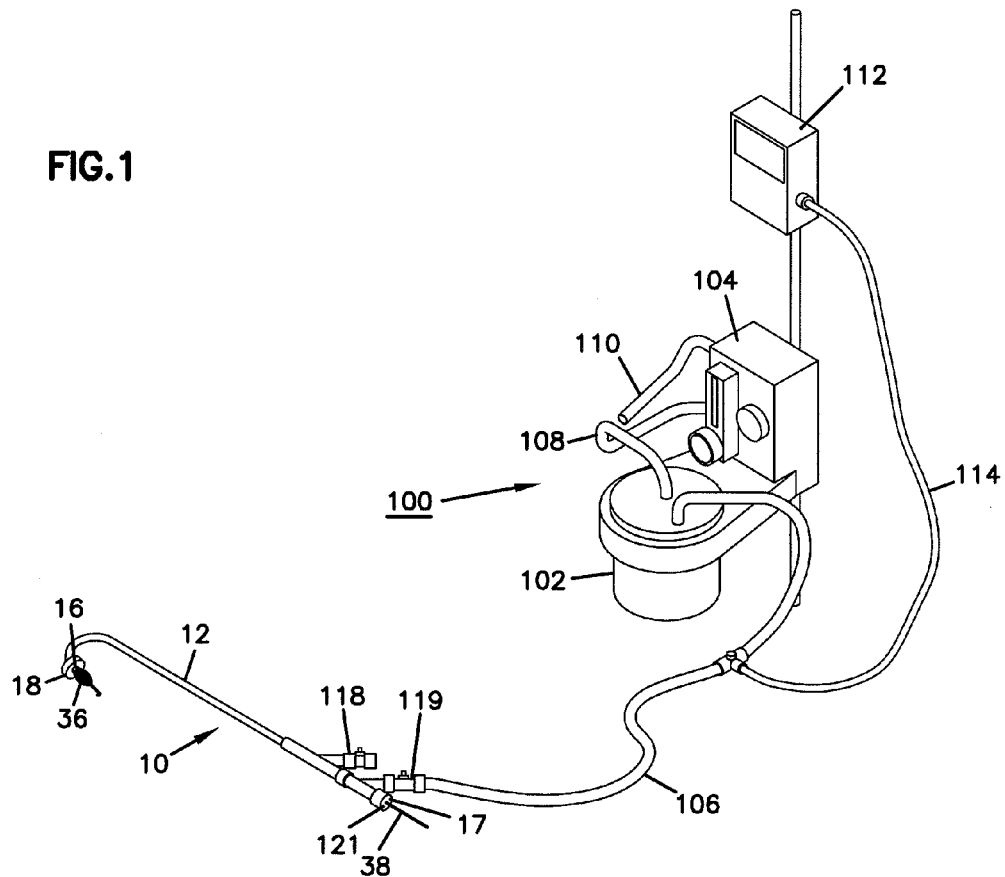
FIG. 1 illustrates a system including a collection catheter according to the present disclosure for collection of blood from a patient's blood vessel and also showing an optional vessel support apparatus.

FIG. 1 shows a system 100 including a collection catheter 10 according to the present invention. In a preferred embodiment, the collection catheter 10 is used to collect blood flow laden with a perfusate or a contrast media which had been injected into a coronary artery for angiography or similar procedures. The collection catheter 10 is to collect blood flow from the coronary sinus before such blood flow can pass systemically to the remainder of the patient's body. While such is a preferred embodiment, the apparatus of the present invention can be used in any blood collection technique including any dialysis or other similar blood collection system. Accordingly, the reference to coronary sinus is illustrative only and can include any other blood vessel.

Figure 1A:
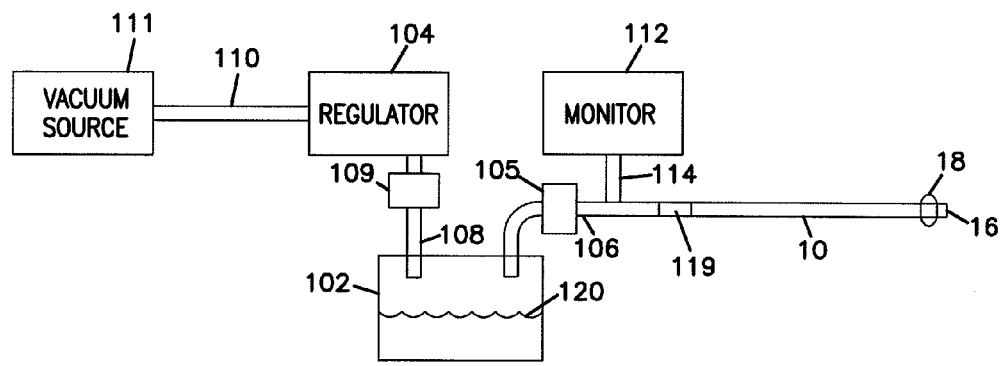
FIG. 1A is a schematic representation of the system of FIG. 1.

In addition to the collection catheter 10, the system 100 includes a collection canister 102 and a vacuum regulator 104 (e.g., negative pressure regulator). The collection canister 102 is sealed from atmospheric pressure. The system of FIG. 1 is schematically shown in FIG. 1A which also illustrates a level of collected blood within the canister 102 and indicated by 120.

Tubing 106 is connects to a port 119 of the collection catheter to communicate with a central collection lumen 26 (as will be described) of the collection catheter 10. The tubing 106 connects the collection lumen 26 to the interior of the canister 102.

Tubing 108 connects the interior of the canister 102 to the negative pressure regulator 104. The negative pressure regulator 104 has a supply tubing 110 to be connected to a source 111 of a vacuum (FIG. 1A). Such a negative pressure (vacuum) source is commonly provided in a hospital or other similar setting.

The system 100 further includes a pressure monitor 112 connected by a tubing 114 to tubing 106. The pressure monitor 112 monitors and displays the pressure within the tubing 106 thereby corresponding to the pressure within the lumen 26 of the collection catheter 10.

A proximal end 17 (FIG. 1) of the collection catheter 10 also includes a port 118 for connection to a source of pressurized fluid (such as air or saline) for pressurizing a sealing balloon 18 (e.g., occluding balloon or annular sealing member) on a distal end or distal tip 16 of the catheter 10, as will be described. The proximal end 17 also includes a port 121 for passing a guide wire or the like into the collection lumen 26.

Figure 2:
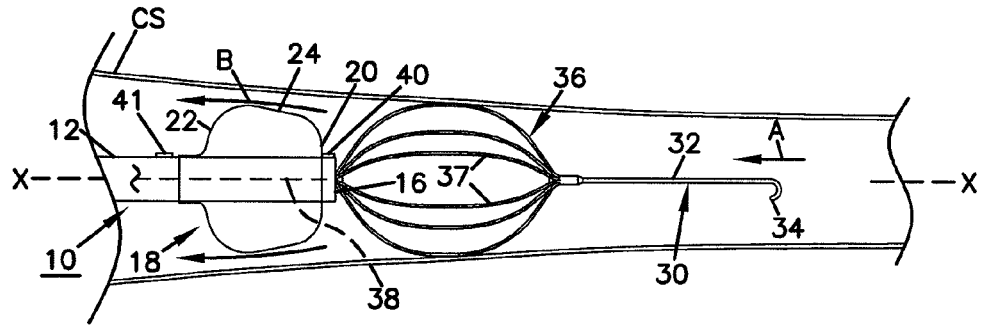
FIG. 2 is a side longitudinal view of a collection catheter of FIG. 1 shown in a coronary sinus of a patient and illustrating spacing between a sealing member and a blood vessel wall when a suction is not applied to a lumen of the catheter.

With best reference to both of FIGS. 1 and 2, the catheter 10 includes a catheter body 12 in the form of an elongated, flexible tubular portion having a proximal end 17 (shown only in FIGS. 1 and 12) and a distal tip 16 (FIG. 2). It will be appreciated that the drawing of FIG. 1 is not to scale and that the length of the catheter body 12 is substantially longer than that shown in FIG. 1 so that the distal tip 16 may be advanced through the vasculature of a patient into a coronary sinus CS while the proximal end 17 remains external to the patient.

As shown in FIG. 2, an annular sealing member 18 is provided in close spacing to the distal end 16. In a preferred embodiment, the annular sealing member 18 is a compliant balloon formed of material which can both conform and stretch as it is inflated. It will be appreciated that compliant balloons are well-known in the art and form no part of this invention per se.

In the embodiment of FIG. 2, the balloon has a radial distal end 20 of smaller diameter than a radial proximal end 22. As a result, an annular surface 24 between the ends 20, 22 is inclined relative to a longitudinal axis X-X of the catheter body 12. It will be appreciated that this geometry is illustrative only. If desired, ends 20 and 22 can have a common diameter such that the annular surface 24 is parallel to the axis X-X. Surface 24 can also be curved (convex or concave) relative to axis X-X.

Figure 3:
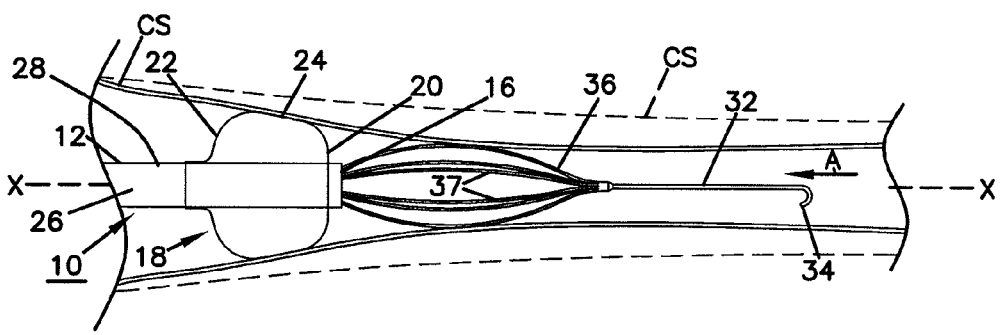
FIG. 3 is the view of FIG. 2 following application of a suction to the lumen of the catheter and illustrating migration of the blood vessel wall into sealing engagement with the sealing member of the catheter.

In FIG. 3, the end 16 is open and communicates with a collection lumen 26 running the length of the catheter body 12. The collection lumen 26 communicates with port 119 (FIG. 1). An inflation lumen 28 is provided in the wall thickness of body 12 for admitting an inflation fluid into the balloon 18. Inflation lumen 28 communicates with port 118 (FIG. 1).

In the figures, the catheter 10 is shown used in combination with an optional vessel support device 30. The vessel support 30 includes a long flexible distal end 32 with a curved tip 34. The distal end 32 and curved tip 34 may be formed in accordance with conventional techniques for forming well-known guide wires to atraumatically advance through a patient's vasculature.

A vessel support cage 36 connects the distal end 32 (e.g., distal wire portion) to a proximal wire portion 38 (FIG. 2). The cage 36 is made up of a generally circular array (around axis X-X) of flexible elastic struts 37 (such as nitinol or other elastic material suitable for use in a blood vessel). As will become apparent, the cage 36 prevents the collapse of the coronary sinus (CS). Further, the positioning of the cage 36 within the coronary sinus provides positioning stability to resist axial movement of the cage 36 relative to the coronary sinus. As a result, the cage 36 is a convenient tool for maintaining a positioning of the catheter 10 within a coronary sinus CS.

In use, the vessel support 30 is advanced into the coronary sinus CS through any suitable means to the position shown in FIG. 2 with the cage 36 abutting opposing surfaces of the coronary sinus CS. In FIG. 2, normal (or antegrade) blood flow is illustrated by the arrow A indicating a direction of normal blood flow through the coronary sinus CS towards the right atrium (not shown). Following such placement, the catheter 10 is advanced over the wire portion 38 of the vessel support until the distal tip 16 abuts the cage 36.

During advancement, the sealing balloon 18 is fully deflated. Following such advancement, a physician may inflate the balloon 18. The balloon 18 is not inflated to such an extent that it abuts against the opposing wall of the coronary sinus CS. Instead, as illustrated in FIG. 2, the balloon 18 is only inflated partially such that an annular flow path is defined between the opposing surfaces of the annular surface 24 and the coronary sinus CS. This flow path is illustrated by the arrows B in FIG. 2.

In the absence of suction applied to the collection lumen 26, blood flow within the coronary sinus CS flows around the balloon 18 to the right atrium. The collection lumen 26 may be primed with saline or the like to avoid loss of suction blood flow from the coronary sinus CS into the collection lumen 26.

By monitoring pressure on the pressure monitor 112, a physician can determine if the balloon 18 is over inflated such that it is sealing the coronary sinus CS when no suction is applied to collection lumen 26. If such over inflation is monitored, the balloon 18 may be slightly deflated until the physician is assured that the balloon 18 is residing in the coronary sinus CS in a non-occluding manner. Alternatively, pressure sensors 40, 41 (shown only in FIG. 2) may optionally be provided on catheter body 12 on opposite sides of balloon 18. A pressure differential between sensors 40, 41 indicates occlusion of the coronary sinus CS. Following such placement, the physician may operate the vacuum regulator 104 to selectively apply suction to the collection lumen 26. Application of such suction causes the coronary sinus CS to at least partially collapse such that the surfaces of the coronary sinus CS opposing the surface 24 migrate against the surface 24 in sealing engagement. This causes blood flow within the coronary sinus CS to flow completely into the lumen 26. Further, such sealing engagement minimizes retrograde flow from the right atrium past the balloon 18 to the distal end 16. Such sealing engagement is illustrated in FIG. 3. The tendency of the coronary sinus CS to collapse is utilized as an advantage to result in sealing of the coronary sinus CS against the sealing member 18. As a result, sealing naturally occurs when suction is applied. No additional inflation or deflation of the balloon 18 is required.

The timing of the application of suction to the lumen 26 is preferably timed to result in collection of a contrast media injected into a coronary artery. For example after a set time (about 3-6 seconds) after injection of a contrast media into a coronary artery, the suction can be applied to the lumen 26. Alternatively, the patient's electrocardiogram may be monitored and suction may be applied a fixed number (e.g., 5) of heart beats following such injection. If desired, a detecting element can be provided at the tip 16 or elsewhere within the system to detect the perfusate or contrast media resulting in activating application of suction to the lumen 26. For example, pressure sensor 40 in FIG. 2 could alternatively be a contrast media sensor.

Blood drawn into the collection lumen 26 is collected in canister 102. After collection, the blood may be discarded. Alternatively, the blood may be passed to any suitable treatment apparatus (not shown) for removal of undesired constituents within the collective blood. The treated blood is then returned to the patient.

The amount of suction provided to the lumen 26 is at a high pressure (e.g., —600 millimeters of Hg) to ensure removal of blood from the coronary sinus. The coronary sinus CS is a very fragile vessel. In response to such suction, the vessel is inclined to collapse. Collapse of the vessel may be avoided by the vessel support 30. FIG. 3 illustrates the cage 36 distal to the tip 16 preventing complete collapse of the coronary sinus. Instead, cage 36 narrows in diameter (resulting in axial lengthening) but resists complete collapse of the coronary sinus CS or invagination of the vessel tissue into the distal lumen opening.

Figure 4:
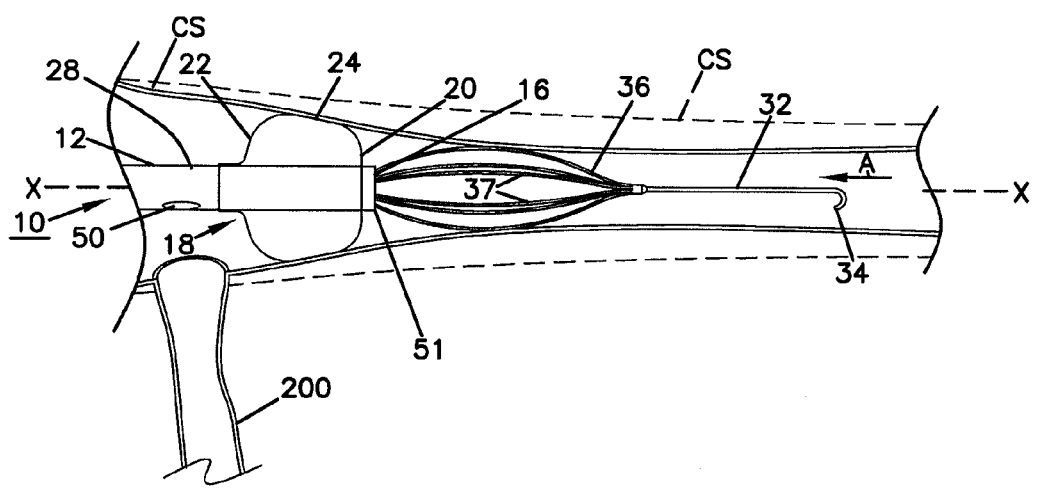
FIG. 4 is a side longitudinal view of a collection catheter incorporating a port proximal to the sealing member (balloon) and illustrates the position of a coronary vein entering the main blood vessel near the proximal port.

The design shown in FIGS. 2 and 3 can effectively seal and remove contrast or other perfusate arriving at the distal tip of the catheter. However, the apparatus would not collect any perfusate or contrast entering the coronary sinus through a vein(s) located proximal to the sealing member or balloon. In FIG. 4, a coronary vein 200 is shown entering the coronary sinus proximal to the occluding balloon 18 and a distal inlet port or distal lumen opening 51. In this embodiment, a port 50 has been provided into the lumen of catheter 10. The port is located proximal to balloon 18 and in the vicinity of the proximally located coronary vein 200. The port is positioned on the circumference of the catheter at a position to locate it near the opening of the proximal vein. The specific position of the port 50 on the circumference of the catheter 10 could be based on the preformed curvature of the catheter. The curvature of the catheter is used to aid in inserting the catheter into the coronary sinus from either a superior or inferior approach. Once the catheter is positioned in the coronary sinus, the shape of the catheter 10 would position the proximal port 50 in an inferior location near the proximal vein 200.

The relevant portion of the perfusate or contrast entering the proximal port 50 compared to the lumen opening 51 at the distal tip is determined by the comparative size of the two openings. In FIG. 4, the proximal port 50 is a diameter that allows a specific percentage of the total flow during application of suction to come through port 50 while the remaining percentage enters through the distal lumen opening 51. The relevant size of the two openings into the collection lumen 26 can be adjusted to provide a desired contribution through each port. The proximal port can also be made up of two or more smaller ports whereby the total size of the ports will be a determinate in the proximal contribution to total flow. Additional ports may also be added to the distal area of the catheter. Again the total surface area of all distal ports will be a determinate in the distal contribution to total flow.

Figure 5:
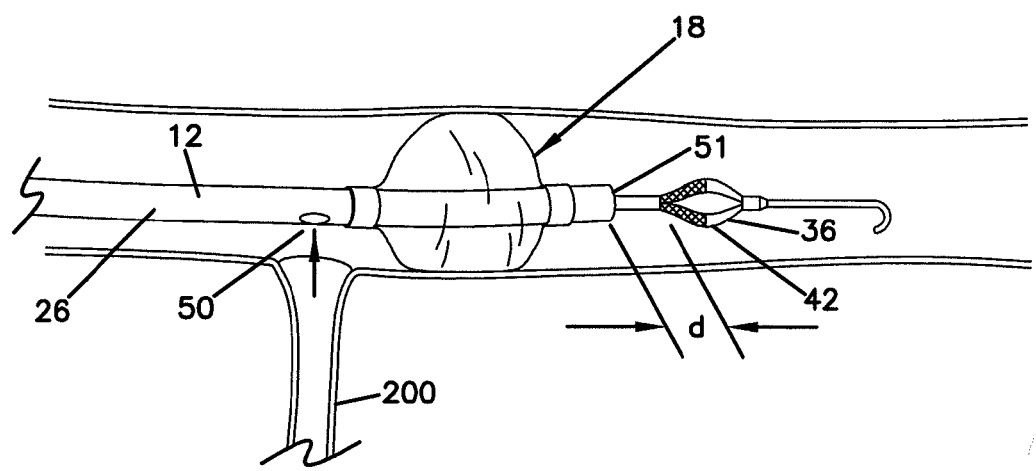
FIG. 5 is a side longitudinal view of a collection catheter of FIG. 4 shown with a restrictive support device in the extended, non-restrictive position.
Figure 5A:
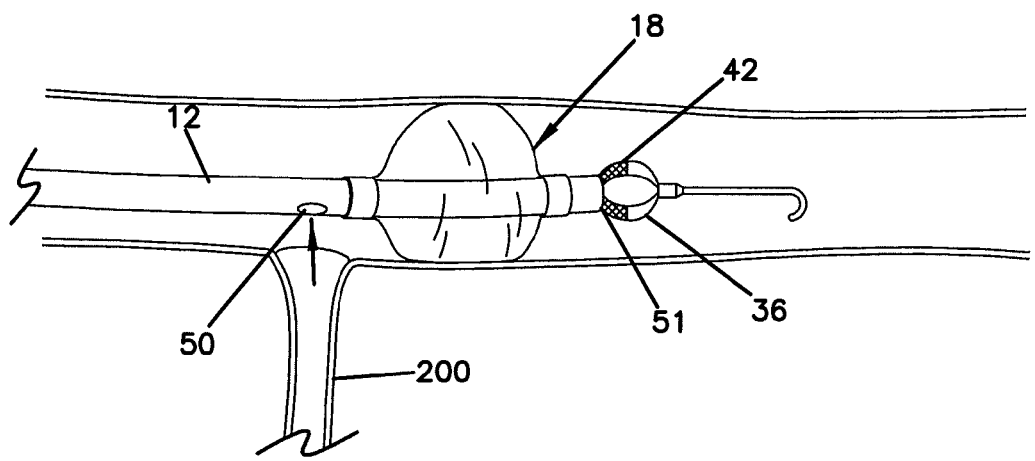
FIG. 5A is a side longitudinal view of a collection catheter of FIG. 4 shown with a restrictive support device in the retracted, restrictive position.

The relative size and number of the proximal and distal ports will determine the contribution of each to total flow through lumen 26 and can be built into the catheter body 12 in a number of configurations. In additional, other embodiment may include means to adjust the functional area of a port or ports to adjust the contribution of each after the catheter has been positioned in the vessel. One such design is shown in FIGS. 5 and 5A. In this embodiment, a cage 36 has a nonporous or partially porous member 42 (e.g., a membrane) attached to the proximal area within the cage. As shown in FIG. 5 the cage 36 is extended distally so as not to impede the flow into the distal lumen opening 51. In FIG. 5A the cage 36 is drawn to abut the distal port thereby reducing the functional diameter of the distal port. This in turn reduces the relative contribution of the distal lumen opening 51 (or distal port) compared to the proximal port 50. In this example, the percentage of the total flow entering lumen 26 through the distal lumen opening 51 decreases with the remaining percentage entering through the proximal port 50 increases. With the greater portion of flow entering through the proximal port 50, a great proportion of perfusate or contrast will be collected from the proximal vein 200.

Figure 6:
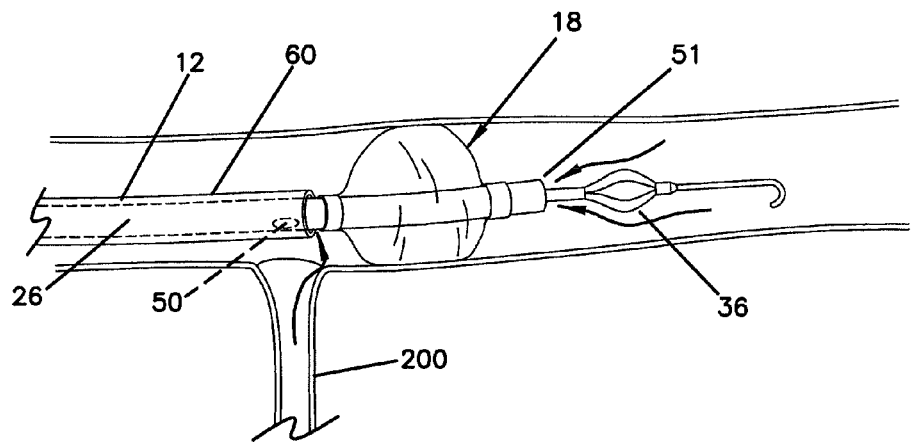
FIG. 6 is a side longitudinal view of a collection catheter shown with a restrictive sleeve over the catheter body and positioned to restrict flow through the proximal port.
Figure 6A:
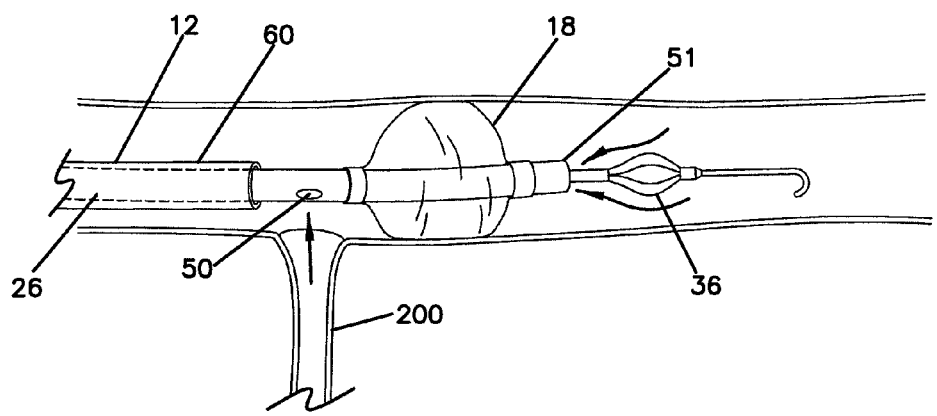
FIG. 6A is a side longitudinal view of a collection catheter shown with a restrictive sleeve over the catheter body and positioned to not restrict flow through the proximal port.
Figure 6B:
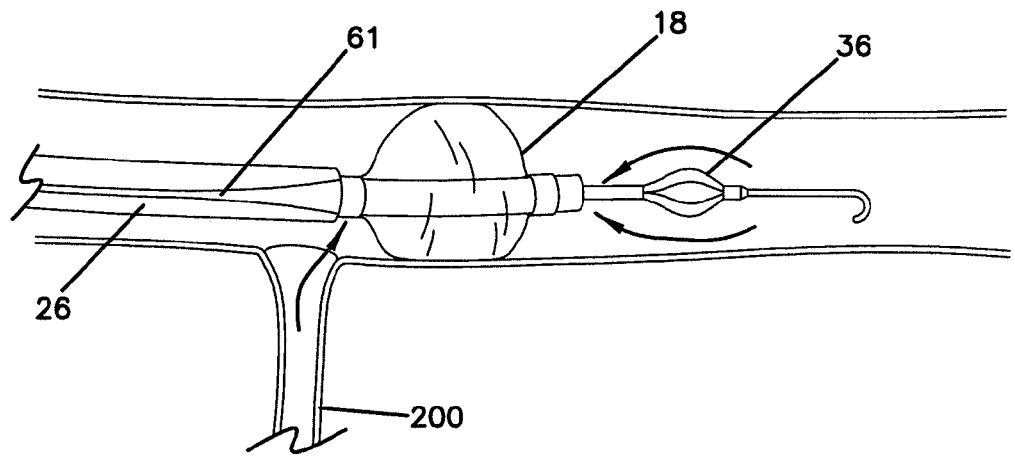
FIG. 6B is a side longitudinal view of a collection catheter shown with a restrictive mechanism within the lumen of the catheter body and positioned to restrict flow through the proximal port.

Other embodiments to adjust the functional area of the proximal and distal ports can be envisioned. One such embodiment, shown in FIGS. 6-6A, would include an adjustable outer sleeve or sheath 60 located around the catheter body 12. The sleeve could be positioned to block part or all of a proximal port 50 or a number of ports if multiple ports are used within the proximal region of the catheter. FIGS. 6 B-C show an adjustable means to block the desired proximal flow that could be incorporated into a structure 61 that is moveable within the collection lumen 26 but does not significantly impede flow through the catheter lumen.

Alternately, the cage 36 can be positioned internally to restrict flow through the proximal port(s) as well. The presence of the cage strut in proximity to the opening will act as a flow restrictor. Also, features may be added to increase the profile of the cage strut and thereby further restrict flow such as beads, flats or shrink tubing. This flow restricting feature can be engaged either by pushing or pulling the inner member relative to the catheter. In addition to engaging these features for aspiration control, this methodology may be employed to facilitate injection of media through the catheter lumen without proximal port leakage as in the case of a venogram.

Figure 7:
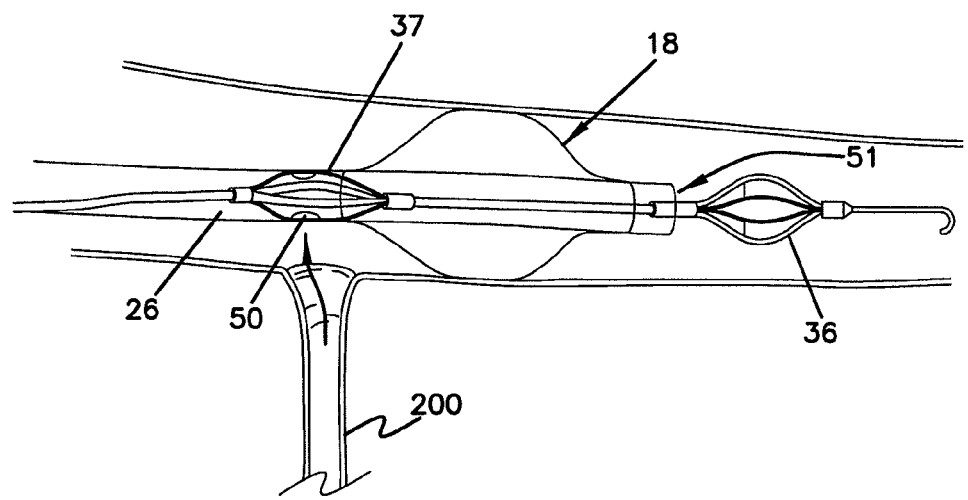
FIG. 7 is a side longitudinal view of a collection catheter of FIG. 4 shown with a restrictive support device positioned within the catheter lumen and positioned to restrict flow through the proximal port.
Figure 7A:
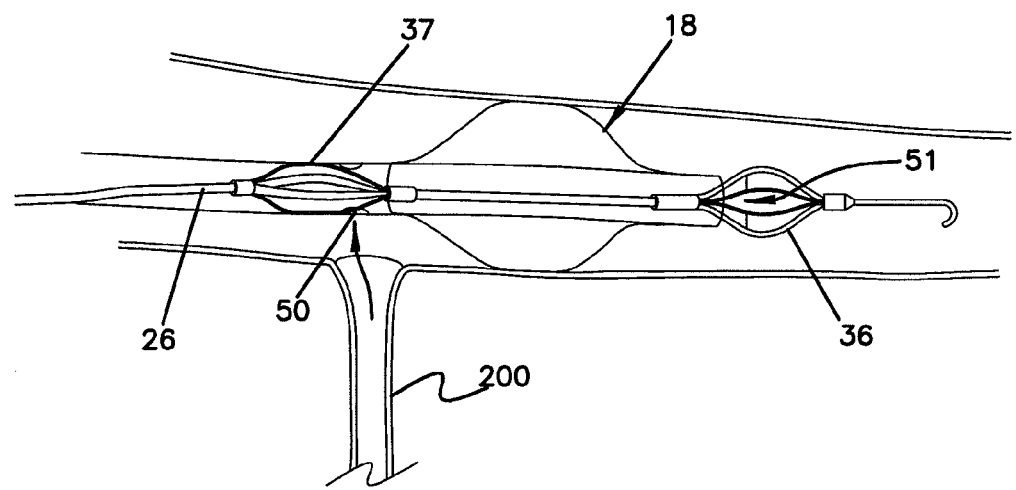
FIG. 7A is a side longitudinal view of a collection catheter of FIG. 4 shown with a restrictive support device positioned within the catheter lumen and positioned to not restrict flow through the proximal port.
Figure 7B:
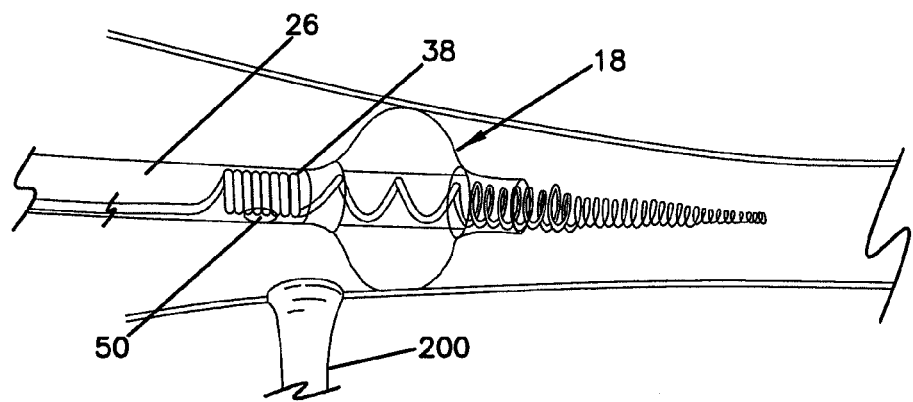
FIG. 7B is a side longitudinal view of a collection catheter of FIG. 4 shown with a restrictive support device positioned within the catheter lumen and positioned to restrict flow through the proximal port.

Another embodiment to adjust the function area of the proximal and distal ports is shown in FIGS. 7-7B. In this embodiment a modification to the vessel support cage 36 is used to partially restrict the proximal port 50. The support cage 36 incorporates a second cage structure which does not significantly impede flow through the catheter's collection lumen 26 but can be positioned to abut the proximal port 50 thus restricting the flow through that port. The support cage structure could be constructed of flattened bands to facility occlusion of the proximal port 50.

Figure 7C:
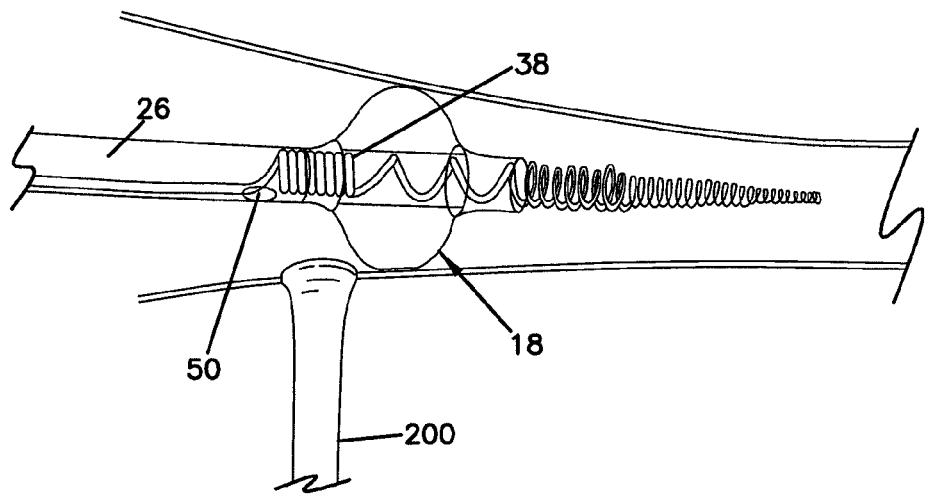
FIG. 7C is a side longitudinal view of a collection catheter of FIG. 4 shown with a restrictive support device positioned within the catheter lumen and positioned to not restrict flow through the proximal port.

The support cage 36 could also incorporate a lumen at the site of the proximal port 50, as shown in FIG. 7 B-C. Blood could flow through the lumen of the support cage 36 without severely impacting flow through the collection lumen 26. The support cage 36 could be positioned to occlude or restrict flow through the proximal port 50 (FIG. 7B) or positioned so as not to restrict flow through proximal port 50 (FIG. 7C).

Figure 8:
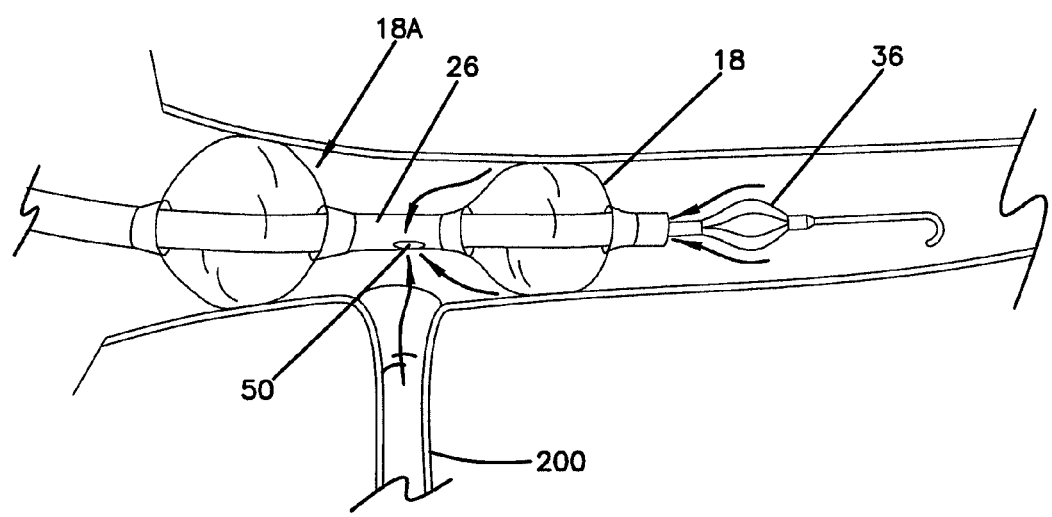
FIG. 8 is a side longitudinal view of a collection catheter shown with a restrictive member positioned proximal to the proximal port to isolate flow from the proximal vein to flow into the lumen of the collection catheter.

In another embodiment, as shown in FIG. 8, a flow restricting device, such as a balloon or membrane 18A located proximal to the proximal port 50, can be utilized to limit the amount of blood not containing perfusate (i.e. retrograde flow of blood from the right atrium). The flow restricting device can be used to isolate the vein(s) that enter the coronary sinus proximal the distal balloon. This flow restricting device can be activated by the user through balloon inflation or the opening and closing of ports in the membrane or other similar mechanism prior to activation of the vacuum system. During active collection the flow restricting device will restrict the retrograde flow of blood that does not contain the perfusate into the proximal port.

There is further a need to determine the blood flow contribution from vein(s) entering proximal to the sealing member, for example near the coronary sinus ostium. Such venous determination could be performed by a sensing system that could measure the contribution of the veins distal and proximal to the sealing member. The sensing system would ideally be able to function in real time, using analog perfusates that are less toxic than the target perfusate—for example, saline in place of contrast media. This would allow a confirmatory setup run to adjust the relative flow from the distal and proximal ports of the catheter.

One method to assess the relative contribution of the distal and proximal veins would be to occlude the proximal port through an apparatus embodiment previously described in this application. An analog perfusate (saline) would be injected at the coronary arterial site and the system would be activated to remove the analog perfusate entering the coronary sinus region. A real time determination of the amount of analog perfusate collected would be determined. The distal port would next be occluded, the proximal port opened and the procedure repeated. Comparing the levels of analog perfusate collected through the proximal and distal ports provides a measure of the relative contribution from distal and proximal veins. Using this information, the proximal and distal port patency would be set to correspond to the contribution of the distal and proximal veins. This should collect the relative proportion from the distal and proximal veins, thus maximizing the contrast removal potential of the system. One could also open the proximal port only if the amount of analog perfusate collected through the distal port falls below a threshold. This would indicate that the proximal vein(s) is contributing a significant portion of the venous blood flow which cannot be captured through the distal port(s). Increased collection could be verified once the proximal port is opened.

The examples and embodiments presented above describe a catheter with a sealing member that becomes occlusive upon a negative pressure being exerted on the vessel. However, the incorporation of proximal ports to collect blood flow veins proximal to the sealing member could also be used with various types of sealing members. This could include sealing balloons that are inflated and deflated with each activation of the system. It also could be incorporated into catheter systems that are non-occlusion but have catheter members that restrict or funnel distal blood flow into the catheter lumen.

Figure 9:
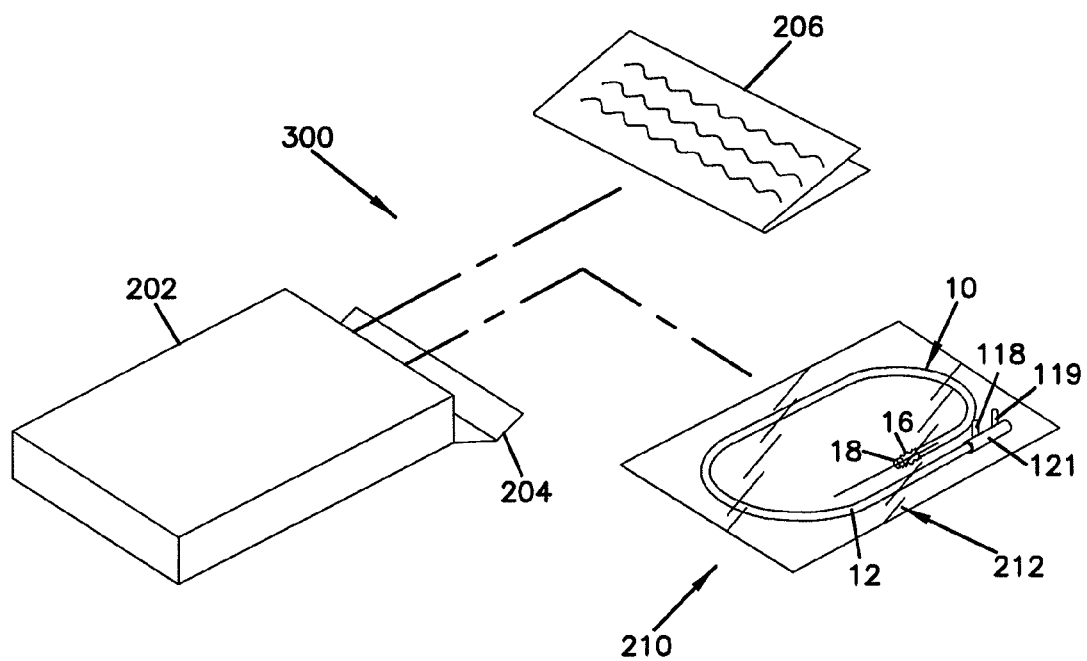
FIG. 9 is an exploded perspective view of a kit according to the present disclosure.

The use of an occlusive or restrictive member distal to the proximal ports would also reduce the blood flow velocity in the regional of the proximal vein(s) and proximal port(s). This slowing of regional blood flow would facilitate the collection of flow from the proximal vein(s) into the collection catheter through the proximal port(s), In a preferred embodiment, the catheter 10 is packaged as a kit 300 shown in FIG. 9. The catheter 10 and its component parts of formed of plastic or other suitable material for placement in human vasculature. The catheter 10 is sized to be advanced through the vasculature with the tip 16 residing in a vein such as a coronary sinus CS. The catheter body 12 is sufficiently flexible and the tip 16 is sufficiently atraumatic to permit such advancement as is known in the art. The materials of the catheter must be appropriate to withstand the rigors of sterilization and meet all biocompatibility requirements as is known in the art.

The catheter 10 is shown in FIG. 6 as contained in a coiled configuration in a clear plastic pouch 212 which is sealed with its contents sterilized for human clinical use. The pouch 212 is contained is a suitable container such as a cardboard box 202 with closure lid 204.

Also contained within the box 202 is a printed sheet containing instructions 206 for use. These instructions 206 would include, in at least summary format, directions of use of the particular catheter and/or system. For example, a user may be instructed to place the distal tip 16 of the catheter in a blood vessel (e.g., coronary sinus CS) with the balloon 18 inflated to be spaced from the vessel wall to permit blood flow past the balloon 18. When desired to collect blood with the catheter 10, suction is applied to the lumen 26 of the catheter 10 to draw the wall of the blood vessel into sealing engagement with the balloon 18.

Figure 10A:
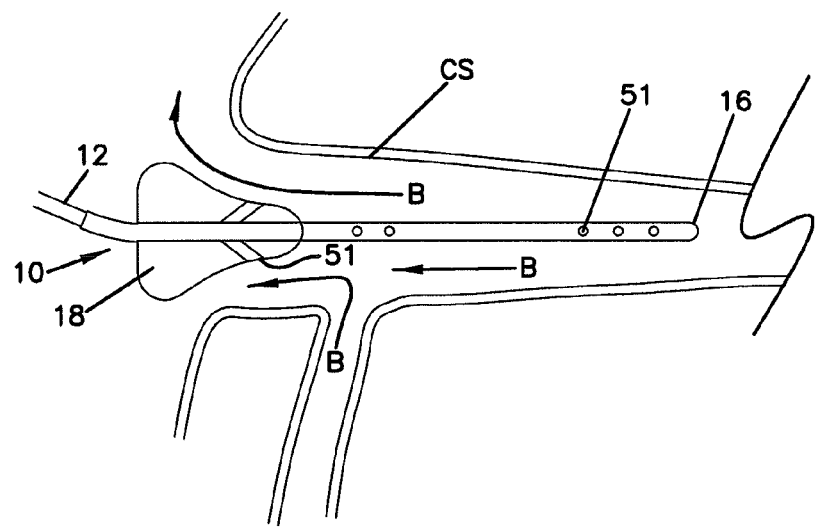
FIGS. 10A and 10B are side longitudinal views of a collection catheter that may be positioned within proximity of an ostium of a vessel; such as, for example, the ostium or orifice of the coronary sinus within the right atrium.
Figure 10B:
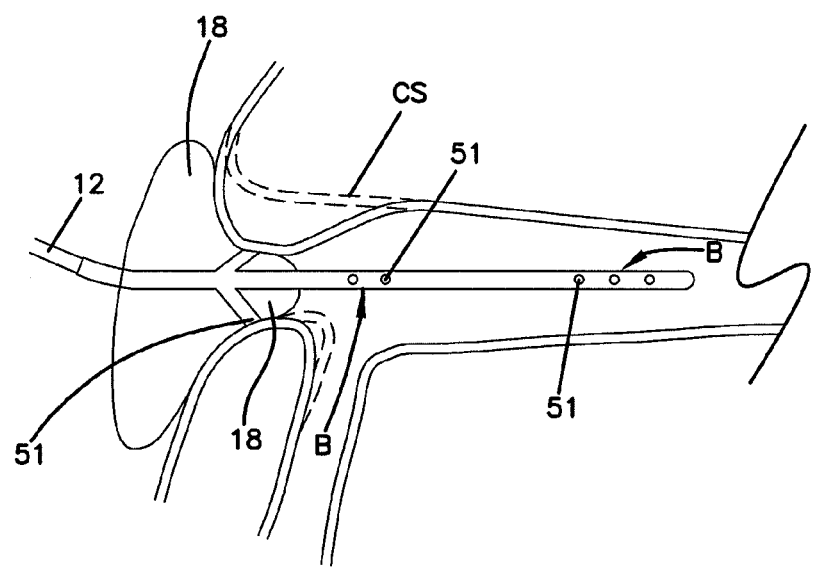

A further example of a collection catheter 10 and its use may be found in FIG. 10. The figure illustrates the placement of a collection catheter wherein the anatomical limitations of the vessel may be best managed by placement of a sealing member 18 of the catheter in proximity of the ostium of the vessel, for example, the orifice of the coronary sinus of the right atrium of the heart. Shown in FIG. 10, the sealing member 18 of the collection catheter may be placed in close proximity of the ostium wherein the distal portion of the catheter intubates the coronary sinus. In this case, application of suction to a collection system of FIG. 10 may draw the sealing member 18 of the catheter into at least partial sealing engagement with the tissue surrounding the ostium. Release of suction would provide for antegrade blood flow from the coronary sinus into the right atrium. It can be appreciated that, upon deployment, sealing member 18 could be of various forms (irregular, curved, anvil shaped, etc.) to accommodate the purchase of the sealing element within, and generally around, the ostium of the vessel when suction is applied to a evacuation/collection lumen 26. One exemplary shape of a sealing member/balloon 18 may be found if FIG. 2. FIG. 10A illustrates a collection catheter 10 before expansion of the sealing member 18 and before application of suction. FIG. 10B shows the collection system after expansion of the sealing member 18 and the activation of suction. The flow of blood B fluid is illustrated with an arrow in each of the figures. Note that, in this example, inlet ports 51 are positioned into and through the sealing member. Further discussion of this element is disclosed below.

Sealing member 18 of collection catheter 10 may also be of various lengths in order to enhance the sealing and the evacuation of a vessel. For example, the sealing member/balloon could extend substantially longer into a vessel, such as the coronary sinus as illustrated in FIG. 10, so as to provide for a much more extensive contact with the sealing member and the vessel wall. Such contact being described previously as contact surface 24 in FIG. 2. Moreover, an elongated sealing member may at least partially result in increased resistance of flow along an extended sealing member 18 length and thus enhance extraction of fluid through catheter inlet ports (50 and/or 51)

Figure 11:
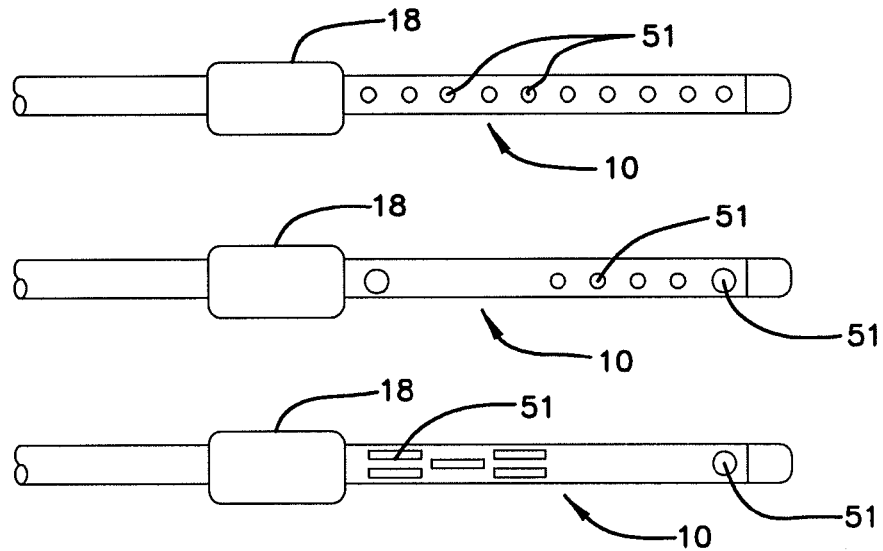
FIG. 11 is a side longitudinal view of various distal portions of collection catheters illustrating a variety of distal inlet configurations.

As previously mentioned with respect to distal inlet ports, it is possible that the selective removal of contrast or perfusate laden blood may be best be performed through the use of more than one distal inlet port. The distal inlet port(s) 51 residing distal the sealing member 18, could take many forms, and be located at various locales along the distal length of the collection catheter 10. FIG. 11 illustrates exemplary distal portion inlet port 51 configurations that may be utilized to improve the selective removal of fluid through the distal portion of the collection system. These constructions may include numerous holes along the length of the distal portion, as well as a variety of size and location of the holes. As illustrated, the distal portion could have holes placed homogenously along the tube, non-homogenously at selective locales, and/or be of various different sizes or shapes (i.e., slots, elliptical, triangular, rectangular). These various inlet attributes may be used in combination, and the examples are to be illustrative and not limiting. The various configurations could provide for selective fluid removal rates along the distal end of the collection catheter as a result of the fluid dynamics created by the various constructions. These distal portion inlet ports could be used in conjunction with other embodiments disclosed herein, such as the restrictive element(s) of FIG. 5A. In this case, the tip of the catheter may be occluded with a restrictive member (cage 36 and member 42) while fluid may be selectively removed through other inlet ports.

Figure 6C:
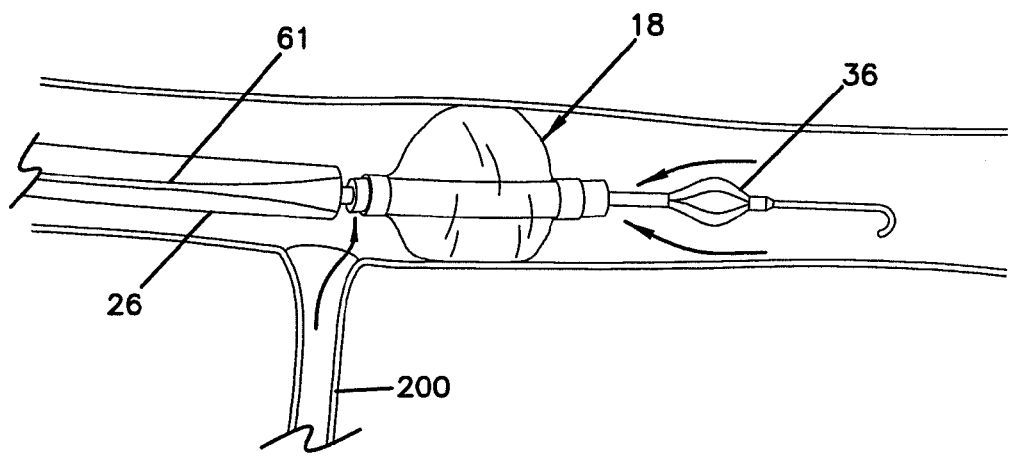
FIG. 6C is a side longitudinal view of a collection catheter shown with a restrictive mechanism within the lumen of the catheter body and positioned to not restrict flow through the proximal port.
Figure 12:
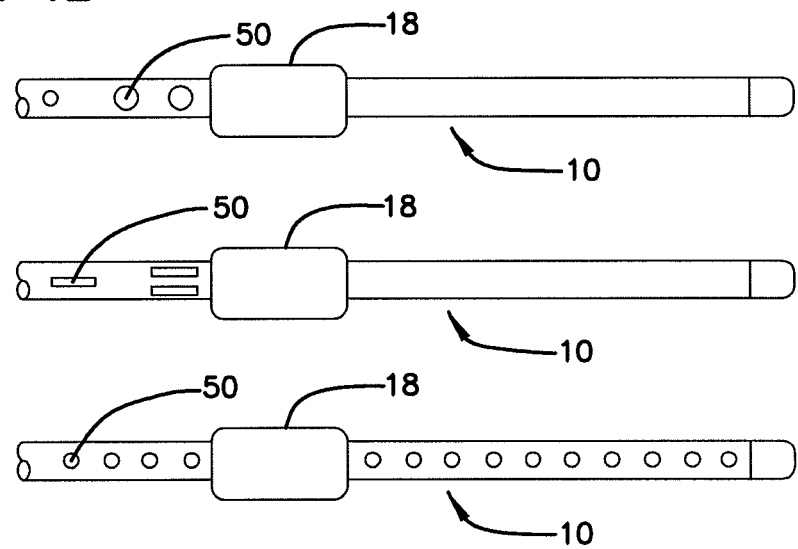
FIG. 12 is a side longitudinal view of various proximal portions of collection catheters illustrating a variety of proximal inlet configurations.

FIG. 12 similarly shows various proximal inlet port (50) constructions that may advantageously used to more effectively extract contrast or perfusate laden blood through a proximal portion of the catheter 10. Illustrated are a variety of ways to evacuate a proximal portion of the collection catheter that may include different number, sizes and locations of the inlet ports 50. In addition, these variations could also be used in combination with other embodiments described herein, such as, for example, the restrictive element of sheath 60 on the collection system of FIGS. 6-6C.

Figure 13:
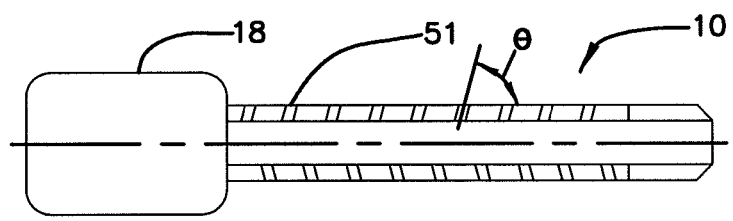
FIG. 13 is a side view of an exemplary alternative configuration of inlets (distal and/or proximal for a collection catheter.

In addition to inlet ports being of different sizes, configurations, and locations along the tubular member, it is possible that the path traveled from the outer surface of the collection catheter to the inner surface of the collection lumen 26 (along an inlet port 50 and/or 51) may have a structure that traverses at an angle θ to the axis of the collection catheter 10, as seen for example in FIG. 13. In this case, one or more of inlet ports (50 or 51) traverse a pathway that is at angle of approximately 20 to 70 degrees from the longitudinal axis of the tubular member. Traversal of different angles through the wall of catheter body 12, into collection lumen 26 may vary the flow dynamics of the removal of fluid from the vessel when suction is applied. Moreover, different configurations may contribute to the sealing of the catheter 10 to the vessel wall. The variations in constructions of ports and placement along the collection catheter may enhance the extraction of fluid and/or sealing effect, and the example given is only to be illustrative.

Inlet ports may be advantageously located along the collection catheter tubular member so as to optimize fluid flow and selective, or differential, extraction of fluid from the vessel. In addition, the port configurations may also be utilized to further enable and/or enhance sealing of the sealing member to the vessel. Moreover, variations of the locations and configurations of the inlet ports may also provide differences in flexibility along the catheter so as to enhance, for example, the ability to circumvent tortuous vasculature.

Figure 14:
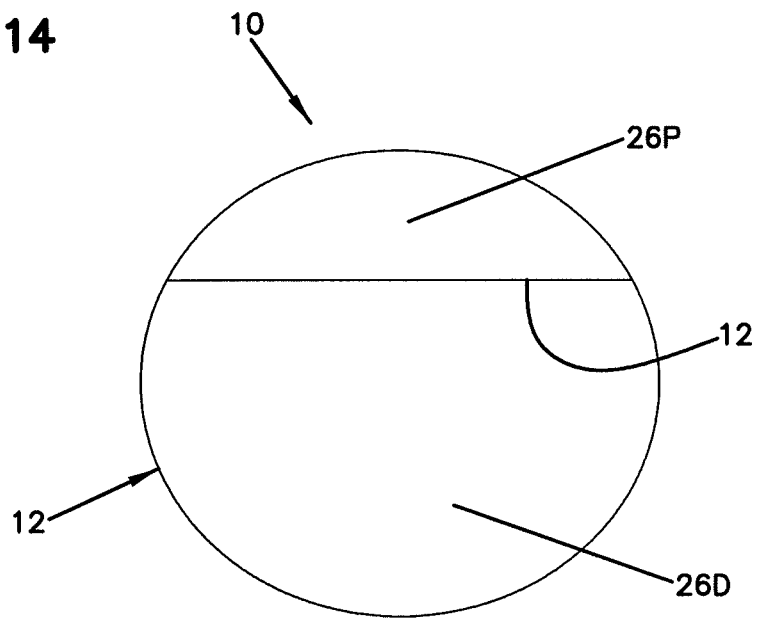
FIG. 14 is a cross-sectional view of an alternative construction drawn across the body of a tubular collection member wherein there may be at least two collection lumens.

Although a single, collection lumen 26 has been disclosed for the collection of fluid from both a distal and a proximal portion of a catheter (with a sealing member located in between), an alternative construction might include two or more collection lumens. Multiple, separate collection lumens 26 may provide for increased selectivity in the extraction of fluid from two or more regions on the collection system. FIG. 14 shows an exemplary cross-sectional illustration (across the body of the tubular member) wherein there is a separate proximal inlet port removal lumen 26P and a distal inlet port removal lumen 26D within the collection catheter. Multiple extraction lumens 26 may provide better control over the extraction of fluid through the respective inlets ports (50 and/or 51). Both lumens may be configured to be attached to a single vacuum/suction source at the proximal portion of the tubular member. Alternatively, each lumen could be configured to be connected to separate suction sources. Moreover, the use of two collection lumens is only illustrative and any combination of lumens could be utilized to effectively extract fluid and/or provide suction from different portions of the collection catheter. As an example, a collection catheter 10 could be constructed with three collection/extraction lumens wherein two of the lumens 26 principally act to enhance variable extraction of fluid from the vessel in the distal and proximal portions, whereas, one of the lumens 26 may be to serve principally enhanced sealing of the collection catheter 10 to the vessel wall. The latter lumen may be configured to enhance sealing with suction independent of other lumens 26 that may provide for collection. Similarly, there may be a variety of collection catheter constructions that are optimized for both extraction and sealing with one or multiple extraction/collection lumens 26 with one or more vacuum sources.

Figure 16:
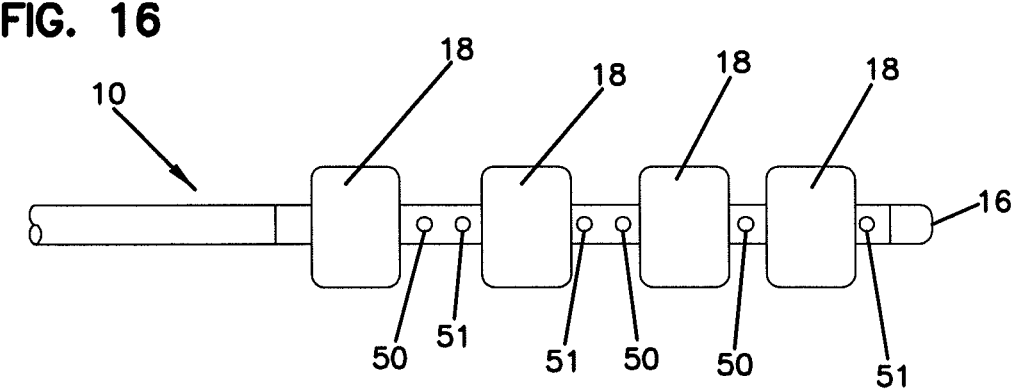
FIG. 16 is an alternative side longitudinal view of an exemplary catheter having a capability of adjusting the relative locale of sealing along the length of the collection catheter.
Figure 17:
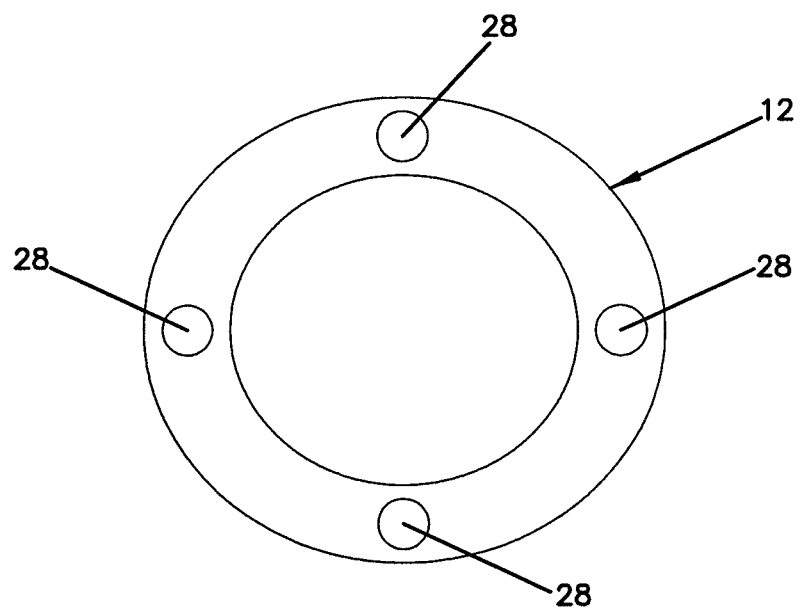
FIG. 17 is a cross-sectional view drawn across the body of the tubular collection member wherein there may be multiple lumens for expanding multiple sealing members independently as, for example, shown in FIG. 16.

As indicated in FIG. 8 and further described by FIG. 16, it can be appreciated that various independent balloons/sealing member structures 18 may be provided along the body of catheter 10 with each balloon (or grouping of balloons) being independently expandable, depending on the locale within the vessel that is intended to be evacuated. FIG. 16 illustrates a collection catheter with, for example, four sealing members 18 that may be independently, or collectively, deployed prior to providing suction to a collection region within a vessel. The independent sealing members 18 may facilitate more selective, or differential, extraction of fluid from a vessel. The collection catheter 10 of FIG. 16 could be equipped with multiple inflation lumens 28 provided within the wall thickness of body 12 for admitting an inflation medium into the various sealing members 18. FIG. 17 illustrates a cross-sectional view of a wall of a body of a catheter 10 which incorporates, for example, four independent inflation lumens 28. It is also possible that sealing member inflation lumens 28 may occupy separate independent structures that provide inflation lumens (e.g., multiple tubes).

Figure 15:
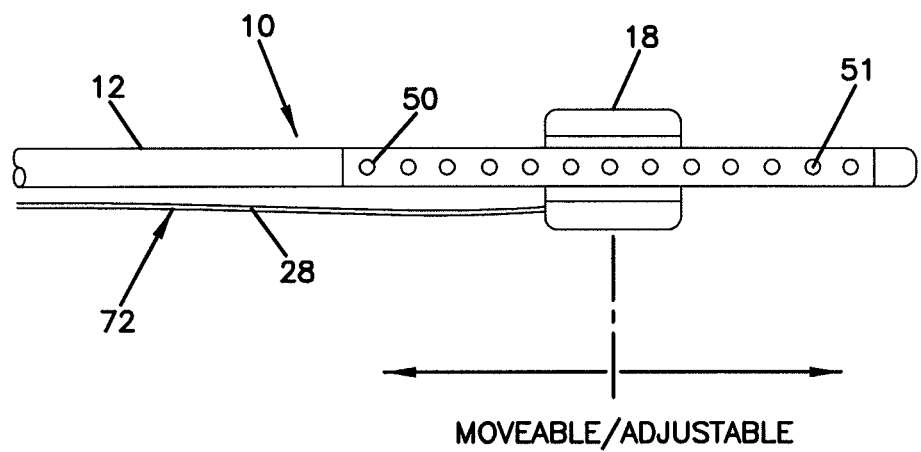
FIG. 15 is a side longitudinal view of an exemplary collection catheter having an adjustable sealing member capable of varying the locale at which it seals within the vessel, along the length of the collection catheter and inlet ports.

An alternative embodiment of a collection catheter is represented in FIG. 15. In this exemplary construction of a collection catheter 10, sealing member 18 is connected to a tube, or guide element 72 to an expansion member (balloon) 18 that resides on a sheath so as to be, at least partially, movable along the length of the tubular portion of the collection catheter 10. Guide element 72 has at least one lumen for the inflation of balloon 18. This construction of a collection catheter allows for independent adjustment of the location of the sealing member after the placement of the distal portion of the catheter into a vessel, such as the coronary sinus. In this regard, the catheter may be capable of varying the locale at which it seals (when activated by the operator) within the vessel, along the length of the collection catheter 10 and inlet ports (50 and/or 51). Although this example utilizes a guide element that is tubular, it is possible to fashion the guide element as a sheath, with or without perforations along its length to accomplish the same goal of varying the locale of a sealing member. Moreover, it is possible to utilize other embodiments described herein in combination with the collection catheter of FIG. 15 to further optimize and/or enhance the sealing and extraction properties of a collection catheter 10. As an example, collection catheter 10 of FIG. 15 could also employ multiple collection/extraction lumens 26 within its body to differentially remove fluid from inlet ports, as further described with respect to FIG. 14

Much of the previous disclosure describes the use of inlet ports (distal and/or proximal) as situated along the length of the tubular member of the collection catheter; however, it is also possible for the inlet port(s) to be situated on, through, into and/or in proximity to the sealing member. FIG. 10 further illustrates one exemplary embodiment of inlet ports 51 passing through a portion of the sealing member. In this illustration, the inlet ports may, among other things, further enhance sealing of the sealing member to the vessel wall.

The above specification provides a complete description of the present invention. Since many embodiments of the invention can be made without departing from the spirit and scope of the invention, certain aspects of the invention reside in the claims hereinafter appended.

What is claimed is:

1. A system for collecting a flow from a blood vessel, comprising:
 a collection member including:
  an elongated, flexible tubular portion terminating at a distal end;
  an annular sealing member movably disposed relative to and about the tubular portion and spaced from the distal end;
  a collection lumen;
  a proximal end adapted to be positioned extracorporealy and connected to a source of suction for applying a suction to the collection lumen;
  at least one distal port in fluid communication with the collection lumen, the at least one distal port being located distal to the sealing member; and
  at least one proximal port in fluid communication with the collection lumen, the at least one proximal port adapted to be disposed intracorporeally and proximal to the sealing member;
  wherein the annular sealing member, by moving relative to the tubular portion, is adapted to proportionate a flow from the blood vessel entering the collection lumen from the at least one distal port and the at least one proximal port, and wherein the annular sealing member is configured to move proximally along the tubular portion so as to alter an inlet area of the proximal port, and wherein the annular sealing member is configured to move distally along the tubular portion so as to alter an inlet area of the distal port; and wherein when the suction is applied to the collection lumen, the flow from the blood vessel is adapted to enter the collection lumen through both of the at least one distal port and the at least one proximal port.

2. The system of claim 1, wherein a position of the annular sealing element alters a number of distal ports and a number of proximal ports exposed along the tubular portion.

3. The system of claim 1, wherein the flow from the blood vessel is further proportionated by at least one of:
   i) a predetermined size of the each of the at least one distal port and the at least one proximal port; and
   ii) a predetermined quantity of each of the at least one distal port and the at least one proximal port.

4. The system of claim 3, wherein the flow from the blood vessel is proportionated by both of the predetermined size and the predetermined quantity of each of the at least one distal port and the at least one proximal port.

5. The system of claim 1, further including a sealed collection container connected to the proximal end for collecting blood from the collection lumen.

6. The system of claim 1, further including a regulator that connects to a source of vacuum, the regulator having an output end connected to the lumen to apply a regulated vacuum to the lumen, the regulator being adjustable to adjust the vacuum, the regulator allowing application of a suction to the lumen in an amount sufficient to draw blood from the vessel through the at least one distal port and the at least one proximal port and into the lumen.

7. The system of claim 1, wherein the collection lumen comprises a first collection lumen in fluid communication with the distal port, and a second collection lumen in fluid communication with the proximal port, and wherein both the first collection lumen and the second collection lumen are in fluidic communication with the proximal end of the collection member and the source of suction.

* * * * *